United States Patent
Kamegai et al.

(10) Patent No.: US 7,157,496 B2
(45) Date of Patent: Jan. 2, 2007

(54) PROPHYLACTIC AGENT OF HYPERTENSION CONTAINING A CONJUGATED FATTY ACID AS AN EFFECTIVE INGREDIENT AND THE USE THEREOF

(75) Inventors: Takeshi Kamegai, Nagoya (JP); Toshio Iwata, Chuo-Ku (JP); Takaya Yamamoto, Nagoya (JP); Teruyoshi Yanagita, Saga (JP); Koji Nagao, Saga (JP)

(73) Assignee: The Nisshin Oillio Group, Ltd., Tokyo-to (JP)

( * ) Notice: Subject to any disclaimer, the term of this patent is extended or adjusted under 35 U.S.C. 154(b) by 0 days.

(21) Appl. No.: 10/866,822

(22) Filed: Jun. 15, 2004

(65) Prior Publication Data

US 2005/0002991 A1    Jan. 6, 2005

(30) Foreign Application Priority Data

Jul. 3, 2003    (JP)    ............................ 2003-191299

(51) Int. Cl.
*A01N 37/00* (2006.01)
(52) U.S. Cl. ...................... 514/560; 514/533; 514/549; 514/552; 554/224; 554/227; 424/807
(58) Field of Classification Search ................ 554/224, 554/227; 514/533, 549, 552, 560
See application file for complete search history.

(56) References Cited

FOREIGN PATENT DOCUMENTS

| EP | 1 174 416 A1 | 1/2002 |
|---|---|---|
| JP | 2002165559 | 6/2002 |
| JP | 2002265985 | 9/2002 |
| WO | 200064854 | * 11/2000 |

OTHER PUBLICATIONS

WPIDS abst. of JP 2002265985.*
WPIDS abstr. of JP2002165559.*
Nagao et al., Biochem. and Biophys. Res. Comm., vol. 306(1), pp. 134-138.*
Nagao et al., Biochem. and Biophys. Res. Comm., vol. 306(1), pp. 134-138.*
Patent Abstracts of Japan, vol. 0072, No. 35 (C-191), Oct. 19, 1983 & JP 58 126770 A (Kiwako Kosuge), Jul. 28, 1983 (Abstract).
Patent Abstracts of Japan, vol. 0122, No. 48 (C-511), Jul. 13, 1988 & JP 63 036744 A (Harumi Okuyama), Feb. 17, 1988 (Abstract).
Atoine J. Vergroesen, "Physiological Effects of Dietary Linoleic Acid", *Nutrition Reviews*, vol. 35, No. 1, Jan. 1977, pp. 1-5.

* cited by examiner

*Primary Examiner*—Deborah D. Carr
(74) *Attorney, Agent, or Firm*—Foley & Lardner LLP

(57) ABSTRACT

The objects of this invention are to prevent or ameliorate hypertension to improve physical constitution and finally to provide feeds, drinks, foods, health food supplements and pharmaceuticals which may be led to the prophylaxis or amelioration of life style related diseases.

A prophylactic or ameliorating agent of hypertension comprising conjugated fatty acids (e.g., conjugated linoleic acid) as effective ingredients.

A feed, food and drink, and health food supplement comprising the conjugated fatty acids described above.

A pharmaceutical comprising the conjugated fatty acids described above.

A method for prophylactic or ameliorating of hypertension in a mammal, which comprises administering to the mammal an effective amount of a conjugated fatty acid for preventing or ameliorating of hypertension in the mammal.

Use of a conjugated fatty acid for preparing a pharmaceutical for prophylactic or ameliorating of hypertension.

15 Claims, 2 Drawing Sheets

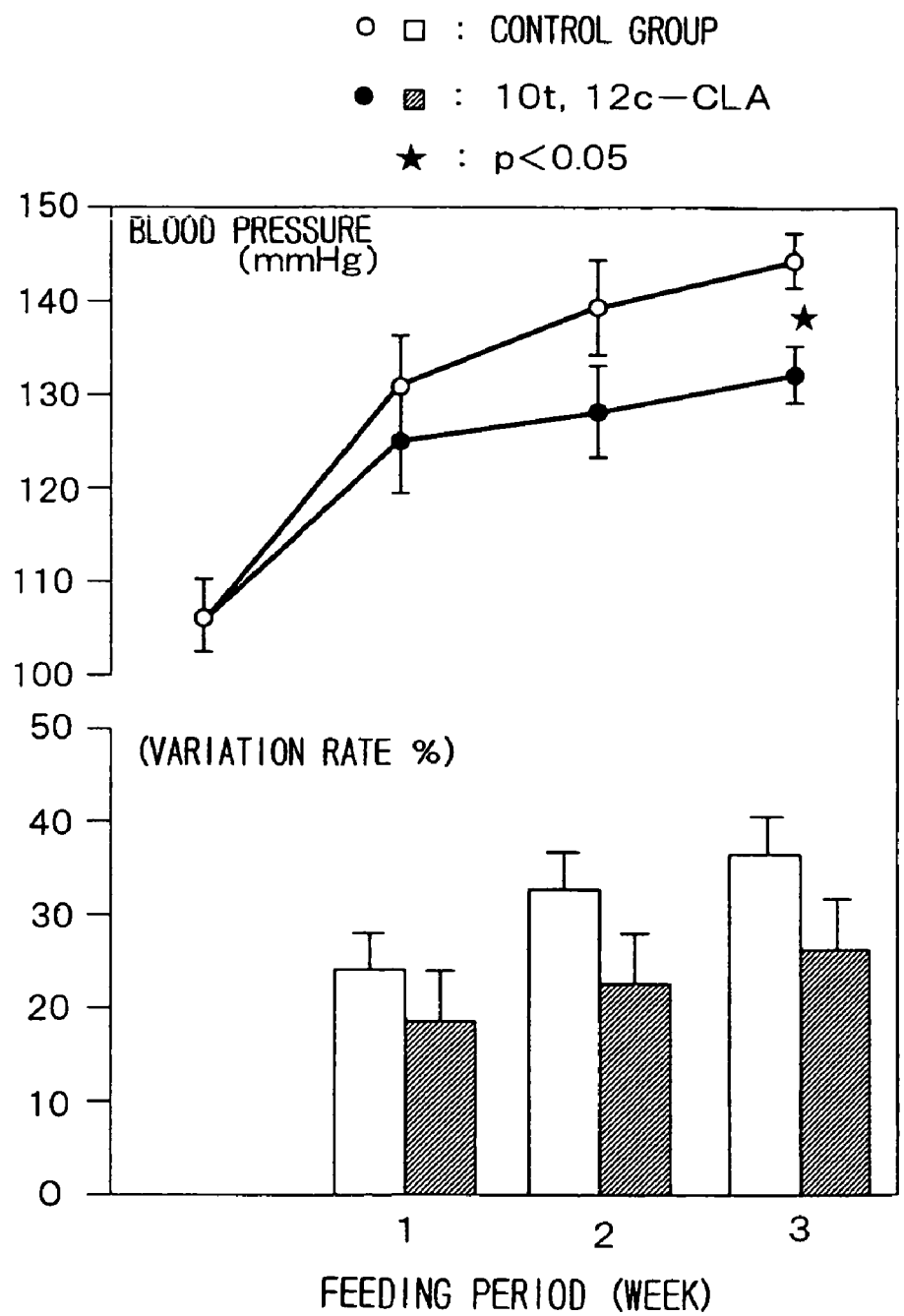
F I G. 1

PROPHYLACTIC AGENT OF HYPERTENSION CONTAINING A CONJUGATED FATTY ACID AS AN EFFECTIVE INGREDIENT AND THE USE THEREOF

BACKGROUND OF THE INVENTION

1. Field of the Invention

This invention relates to the prophylaxis or amelioration of hypertension or life style related diseases, or to the use of conjugated fatty acids, e.g., conjugated linoleic acid (referred to hereinafter as CLA), more particularly to feeds, drinks, foods, health food supplements, and pharmaceuticals which contain the conjugated fatty acids in the form of a free fatty acid, salt, ester fatty acid derivative, or a mixture of the two or more thereof.

2. Background Art

Hypertension refers to blood pressure higher than its normal range, and either of systolic blood pressure of 140 mmHg or more, or diastolic blood pressure of 90 mmHg or more is defined as hypertension (The Japanese Society of Hypertension). Hypertension is divided into secondary hypertension of which the cause has been revealed and essential hypertension caused by genetic or environmental factors. Ninety percent of hypertension is considered to be essential hypertension, in which living factors such as stress, excessive salt intake, overeating, and lack of exercise are strongly involved.

There are now about six hundred million hypertensives in the world, and about three million patients die annually of hypertension as the direct cause of death. It is estimated that the number of hypertensives in Japan reaches about thirty-three millions, which correspond to one-third of the population of the adults. The first rank of the cause of death of Japanese is cancer or malignant tumor, the second rank is cerebral stroke, and the third rank is cardiovascular disease, and the diseases in the second and third ranks are caused primarily by hypertension. Hypertension is the most important risk factor of cerebral stroke, and may cause a variety of circulatory diseases such as cardiovascular diseases, kidney diseases, and arteriosclerosis obliterans. In addition, it has been proved that hypertension is also involved intensively in causing senile dementia. Nowadays when senile populations have been a significant part of the society, it is very important to prevent hypertension in order to anticipate healthy golden years with maintaining QOL (Quality of Life).

Now, it is also possible to remit serious hypertension by developing depressors. Among these agents, Ca-antagonists are the most popularly used in Japan, however these agents may cause tachycardia, palpitatio cordis, or edema. In addition, ACE inhibitors for blocking the action of the renin-angiotensin system which raises blood pressure may cause an unproductive cough.

The prophylaxis or amelioration of hypertension requires the ingestion of a hypotensor over a long period of time, and it is desired to have foods having further regard to safety.

For instance, gamma-aminobutyric acid as a foodstuff exhibits blood pressure lowering effect even at a safe and small dose to allow its ingestion for a long period of time (Japanese Patent Laid-Open Publication No. 10/215,812). However, depressors and drugs, health food supplements, drinks and foods having blood pressure lowering effect have no effect for ameliorating hypertension itself, and thus the original hypertensive state will reappear by the stopping of their administration. In addition, it may enhance the risk of apoplexy or heart diseases that patients discontinue the drug without direction by the physician. Therefore, it is recommended to carry out exercise, diet control, and no smoking, and to make an environment in which no stresses are accumulated, but it is not easy to conduct such countermeasures.

In addition, while the effects of preventing and ameliorating hypertension have been deduced in conjugated trienoic acids (Japanese Patent Laid-Open Publication No. 2002/265985), these effects have not been confirmed, and with regard to CLA as the conjugated dienoic acid, no reports have been described on the influence on blood pressure as far as we know.

SUMMARY OF THE INVENTION

Thus, the objects of this invention are to prevent or ameliorate hypertension to improve physical constitution and finally to provide feeds, drinks, foods, health food supplements and pharmaceuticals which may be led to the prophylaxis or amelioration of life style-related diseases.

The present inventors have carried out intensive investigations for the purpose of accomplishing the objects described above, and as a result thereof, have found that CLA, preferably 10trans,12cis-CLA has a hypotensive effect. The present invention has been accomplished on the basis of the findings.

That is, the present invention includes the following inventions as the gists:

A prophylactic (or preventing) or ameliorating agent of hypertension which comprises a conjugated fatty acid (in the form such as a free fatty acid, salt, ester or fatty acid derivative thereof, or a mixture thereof) as an effective ingredient.

In a preferred embodiment, it is the preventing or ameliorating agent of hypertension, in which the conjugated fatty acid is conjugated linoleic acid (preferably, 10trans, 12cis-isomer).

A prophylactic (or preventing) or ameliorating agent of life-style-related diseases comprising the conjugated fatty acid or the above agent as an effective ingredient.

A feed, food and drink, health food supplement, and pharmaceutical comprising the conjugated fatty acid or the agent.

A method for prophylactic (or preventing) or ameliorating of hypertension in a mammal (including a human and the other animal), which comprises administering to the mammal an effective amount of a conjugated fatty acid for preventing or ameliorating of hypertension in the mammal.

Use of a conjugated fatty acid for preparing a pharmaceutical for prophylactic (or preventing) or ameliorating of hypertension.

BRIEF DESCRIPTION OF THE DRAWINGS

FIG. 1 illustrates graphically the relationship between the blood pressures of the OLETF rats and the feeding period of the diet containing CLA.

Figure 2:
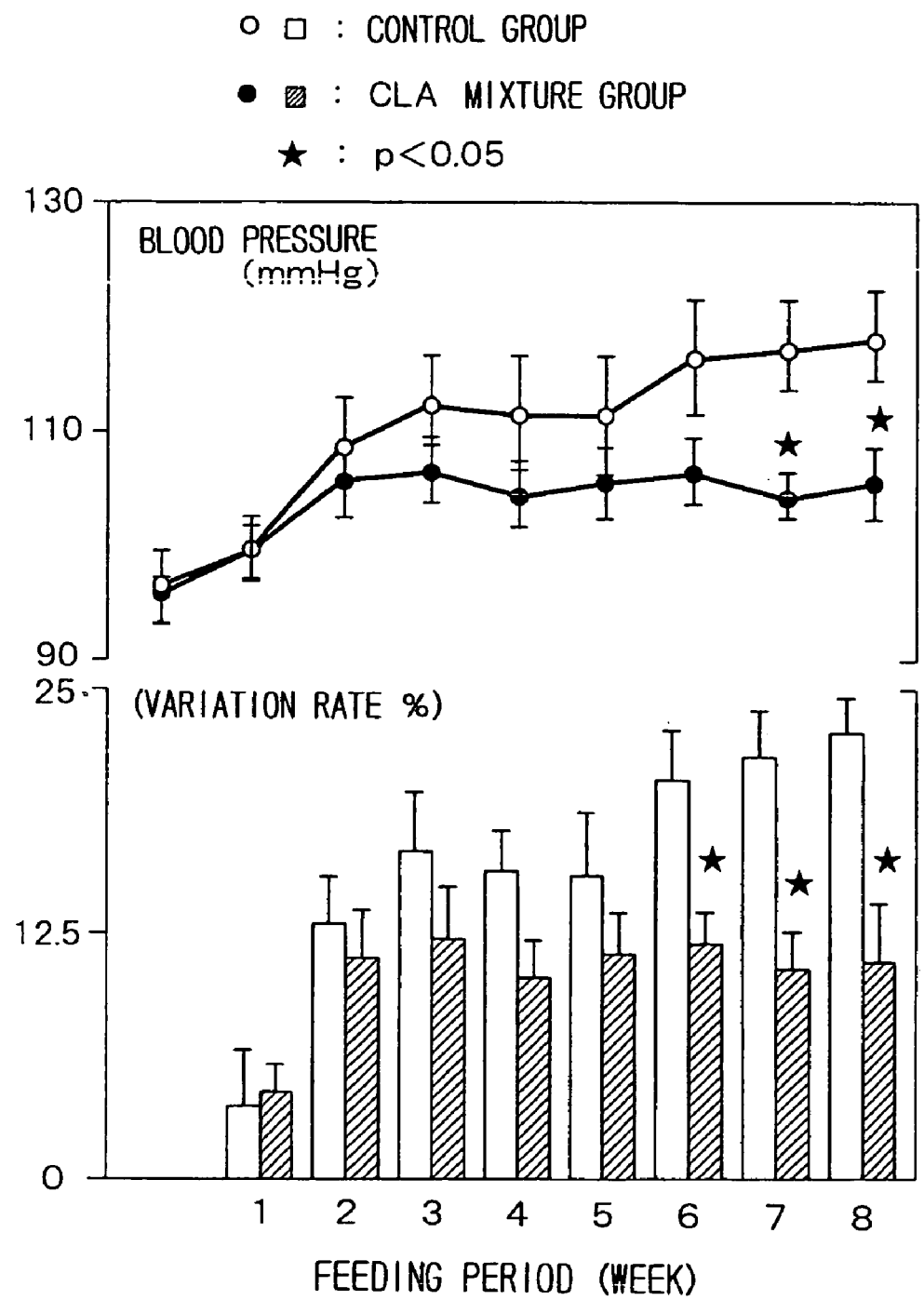

Asterisk(*) shows significant difference between groups at $p<0.05$.

FIG. 2 illustrates graphically the relationship between the blood pressures of the Zucker rats and the feeding period of the diet containing CLA.

Asterisk(*) shows significant difference between groups at $p<0.05$.

DETAILED DESCRIPTION OF THE INVENTION

In the present invention, the use of the conjugated fatty acid may lead to not only the prophylaxis or amelioration of hypertension but also the prophylaxis or amelioration of life style-related diseases.

That is to say, the present invention is a preventing or ameliorating agent of hypertension which comprises a conjugated fatty acid as an effective ingredient, and in the other aspect it is also a preventing or ameliorating agent of life style-related diseases.

The life style-related diseases is defined by The Ministry of Health, Labour and Welfare as the group of diseases in which life-styles such as diet styles, sport styles, recreation, smoking, and drinking are involved in the crisis or progress of the diseases, and include pathologies such as obesity caused by diet, overweight among children and adolescents, dystrophia, cibophobia, diabetes, stomach cancer, colon cancer, gout, dyslipidemia, hypertension, arteriosclerosis, renal calculus, myocardial infarction, gastric ulcer, renal diseases, osteoporosis, periodontitis, alcoholic hepatitis caused by drinking, fatty liver, cirrhosis, liver cancer, lung cancer caused by smoking, chronic bronchitis, pulmonary emphysema, periodontal disease, apoplexy, heart diseases, strain death caused by lack of recreation or sleeping, insomnia, and the like.

The conjugated fatty acids as the effective ingredient of the invention are generally used in the form of a free fatty acid, salt, ester, fatty acid derivative, or a mixture of the two or more thereof.

The salts of the fatty acids include sodium salts, potassium salts, ammonium salts, sodium carbonate salts, magnesium chloride salts, double salts, complex salts, and the like, the esters include, for example, triglyceride, diglyceride, and monoglyceride esters, mono-, di- and poly-alcohol fatty acid esters, sucrose fatty acid esters, sorbitan fatty acid esters, glycerol fatty acid esters, and the like, and the fatty acid derivatives include ascorbic acid derivatives, methyl fatty acids, ethyl fatty acids, acyl chlorides, acyl iodides, acyl bromides, acyl fluorides, and dimers, trimers, polymers of fatty acid, and the like.

The present invention is now described below in detail on the basis of the preferred embodiments.

The typical example of the conjugated fatty acids used in the invention is conjugated linoleic acid, which includes particularly 10trans,12cis-isomer, 9cis,11trans-isomer, and mixtures thereof. The conjugated linoleic acid isomer is preferably the 10trans,12cis-isomer, and desirably the conjugated linoleic acid comprises 5% by weight or more, preferably 40% by weight or more, more preferably 85% by weight or more of this isomer.

A specific example of the conjugated linoleic acid is the one which is obtained by the well-known method using alkali conjugation in which a linoleic acid containing edible oil such as a safflower oil or a sunflower oil or a high-purity linoleic acid such as the one manufactured by Tokyo Kasei Kogyo Co., Ltd. as a material of linoleic acid is converted into a conjugated linoleic acid by the usual alkaline isomerization. For instance, there are known a method in which potassium hydroxide and ethylene glycol are used (Abstract of The 34th Symposium of the Japan Oil Chemist's Society, p. 171 (1995); Standard Methods for the Analysis of Fats, Oils and Related Materials 2.4.16–17), and more preferably a method in which propylene glycol is used as an organic solvent for improving the conjugation rate (Japanese Patent No. 3017108), and the like. For practical use, a mixture of 9cis,11trans- and 10trans,12cis-conjugated linoleic acids is commercially available (e.g. CLA-80, manufactured by Rinoru Oil Mills Co., Ltd.; containing 33.1% of 9cis,11trans-CLA, 33.9% of 10trans,12cis-CLA with remaining of the other fatty acids), and it may be used. The conjugated linoleic acid may also be a mixture of fatty acids obtained from the conjugated linoleic acid containing fats and oils which are produced with microorganisms such as lactic acid bacterium (see, for example, U.S. Pat. No. 6,060,304 in which lactic acid bacterium is used).

The conjugated linoleic acid containing fatty acid obtained by the method described above has a content of conjugated linoleic acid in the range of generally 5–95%, practically 50–85%, and for example 60–80%, and the remaining ingredients are the other fatty acids and the like. The conjugated linoleic acid thus obtained is composed predominantly of the 9cis,11trans- and 10trans,12cis-isomers, with the content of the other conjugated linoleic acid isomers being usually in the range of 4–5%, and the contents of these isomers are approximately equal to each other.

In this connection, the denotation % used herein means % by weight unless otherwise specified or except the case that the denotation % alone signifies a clear meaning.

While the conjugated linoleic acid containing fatty acid obtained by the method described above has a content of the 10trans,12cis-isomer of in the range of about 50%, a variety of the conjugated linoleic acid containing fatty acid can be used having various contents of the isomer including the ranges described above in the present invention. Specifically, by way of example, the conjugated linoleic acid obtained by the usual alkali conjugation described above is subjected to esterification using lipase specific to the 9cis,11trans-isomer with the subsequent combination of known methods such as molecular distillation, enzyme reaction, addition of urea, and the like (see Nagao et al., J. Am. Oil. Chem. Soc., 79, 303–308, 2002) to give a fatty acid containing 50% or more of 10trans,12cis-CLA.

As the above-described method including the selective esterification of the isomers, for instance, as described later in the Examples, selective transesterification of the 9cis,11trans-isomer can be carried out (if necessary, repeatedly) by reacting the mixture of the conjugated linoleic acid isomers obtained by the alkaline conjugation described above and an alcohol such as lauryl alcohol with a lipase such as the one derived from *Candida rugosa* before molecular distillation according to the usual method resulting in the free fatty acid fraction, which is subjected to the addition of urea in ethanol (see, for example, Nagao et al., J. Am. Oil. Chem. Soc., 79, 303–308, 2002) followed by cooling filtration. Furthermore, it is also possible to use the known method by Shimada et al., Ibid., 75, 1539–1543, 1998. It is thus possible to obtain a fatty acid containing 50% or more (generally in the range of about 50–90%) of the 10trans,12cis-CLA according to the method described above. This 10trans,12cis-CLA containing fatty acid contains generally about 5–10% of the 9cis,11trans-isomer with the remaining ingredients being the other fatty acids and the like. In the method above, it is possible to obtain a fatty acid in which the content of the 10trans,12-cis isomer is adjusted to the desired range by appropriately adjusting the reaction conditions such as enzyme concentration, reaction temperature, reaction time, and the like.

On the other hand, as regards the selective transesterification described above, it is possible to obtain a fatty acid containing 50% or less (generally in the range of less than about 50–10%) of the 10trans,12cis-CLA by the 10trans,12cis selective transesterification reaction with lipase such as the one derived from *Pseudomonas* or the like which is specific to the 10trans,12cis-isomer (Japanese Patent Laid-Open Publication No. 2001/169794). This 10trans,12cis-CLA containing fatty acid contains generally about 50–90% of the 9cis,11-trans-isomer with the remaining ingredients being the other fatty acids and the like. In the method above, it is possible to obtain a fatty acid in which the content of the 10trans,12cis isomer is adjusted to the desired range by appropriately adjusting the reaction conditions such as enzyme concentration, reaction temperature, reaction time, and the like.

For practical use, a fatty acid containing the 10trans, 12cis-CLA with high purity is commercially available (manufactured by Matreya Inc.; containing 98% of the 10trans,12cis-CLA, 1.1% of the 9cis,11trans-CLA with remaining of the other fatty acids), and it may also be used.

As described above, it is possible to obtain a fatty acid containing the content of the CLA isomers specified above, that is, the fatty acid containing 10trans,12cis-isomer in the range of 5% by weight or more, preferably 40% by weight or more, more preferably 85% by weight or more (e.g. up to about 90%) in the conjugated linoleic acid.

In the present invention, the above-described conjugated fatty acid (in a preferred embodiment, conjugated linoleic acid) can be used as an effective ingredient of a prophylactic or ameliorating agent of hypertension.

The present invention relates to feeds, drinks, foods, health food supplements comprising the conjugated fatty acids described above. For these uses, in addition to the conjugated fatty acids as the effective ingredient, seasonings such as sodium glutamate, inosinic acid, and the like for improving palatability, and a variety of additives such as tocopherols, flavone derivatives, caffeic acid derivatives, gossypol, sesamol, phospholipids, amino acids and derivatives thereof, saccharides, sugar alcohols, and the like for improving oxidation stabilities may be contained.

Furthermore, various emulsifiers such as polyglycerol fatty acid esters can be incorporated into foods such as breads, noodles, fish cakes, milk beverages, cooling drinks, gums, candies, and the like irrelative to their compatibilities. Also, the above-described foods can be used not only in the liquid state, but also in any forms of powders by the spray-drying according to the usual method, gelatinationg or tablets or the like.

The foods containing the product of the present invention can be incorporated into spreads, margarines, creams, dressings, mayonnaises, cheeses, ice creams, bakery foods, infant foods, soups, prepared foods, and the like, but not limited thereto.

When the prophylactic or ameliorating agent of hypertension according to the present invention is used for foods (including, for example, drinks and feeds), the content of the conjugated fatty acids in the foods is generally in the range of about 0.5–20.0% by weight, and the prophylaxis or amelioration of hypertension is expected by ingesting the conjugated fatty acids in an amount of about 1 mg–10 g, preferably about 0.1 g–10 g per day.

In addition, when the prophylactic or ameliorating agent of hypertension according to the present invention is used for pharmaceuticals, additives including excipients such as glucose and lactose, and pH adjusting agents such as baking soda may be used in addition to the conjugated fatty acids as the effective ingredient. The pharmaceuticals according to the present invention may be used as oral dosages such as tablets, capsules, granules, and powders as well as parenteral dosages such as injections, suppositories, and the like. The pharmaceuticals thus prepared may be used as prophylactic or ameliorating agent of hypertension, and can also be used for applications of the prevention or amelioration of obesity or prophylaxis or amelioration of diseases caused by life-styles. While the dose of the pharmaceuticals is generally in the range of about 1 mg–10 g, preferably about 0.1 g–10 g per day, the efficacy of the pharmaceuticals does not depend on ingestion times such as before, between or after meals, and life-styles. In addition, the number of ingestions per day is not limited, and the required amount can be ingested either in single or several times without significant difference of the effect.

EXAMPLE

The present invention is now described more specifically by referring the following examples, but it is not limited by these examples.

Example 1

Separation of CLA Isomers

Alkali conjugation was carried out by the conventional method with linoleic acid (reagent grade, 98% by weight, Tokyo Kasei Kogyo Co., Ltd) as a raw material and propylene glycol (refer to Japanese Patent No.3017108). CLA obtained was a mixture of CLA isomers comprising 45.1% by weight of the 9cis,11trans-CLA and 46.8% by weight of the 10trans,12cis-CLA. As the first step of purification, the 9cis,11trans-CLA and the 10trans,12cis-CLA were separated. In a two-liter reaction container, to a mixture of 1,000 g of a CLA isomer mixture comprising 45.1% by weight of the 9cis,11trans-CLA and 46.8% by weight of the 10trans, 12cis-CLA and 664 g of lauryl alcohol (1:1 mol/mol) was added lipase derived from *Candida rugosa* in a concentration of 20 U/g of mixture, and the resulting mixture was subjected to selective transesterification at 30° C. for 16 hours followed by molecular distillation according to the usual method to give a free fatty acid fraction in a yield of 516 g (containing 78.1% by weight of the 10trans,12cis-CLA) and a lauryl ester fraction in a yield of 751 g (containing 85.1% by weight of the 9cis,11trans-CLA).

Example 2

Purification of 10trans,12cis-CLA

To 235 g of a mixture of the free fatty acid fraction obtained in Example 1 and lauryl alcohol (1:1 mol/mol) was added lipase derived from *Candida rugosa* in a concentration of 30 U/g of mixture, and the resulting mixture was subjected to selective transesterification at 30° C. for 16 hours followed by molecular distillation according to the usual method to give a free fatty acid and a lauryl ester fractions (the fatty acid fraction of the distillate containing 86.3% by weight of 10trans,12cis-CLA). The distillate fraction of the molecular distillation thus obtained was subjected to the addition of urea in ethanol according to the conventional method and subsequently to filtration under gradual cooling to give 95.7% by weight of 10trans,12cis-CLA.

Example 3

Purification of 9cis,11trans-CLA

The lauryl ester fraction obtained in Example 1 was subjected to hydrolysis in the presence of alkali, NaOH, according to the conventional method. To 760 g of a mixture of the free fatty acid fraction thus obtained and lauryl alcohol (1:1 mol/mol) was added lipase derived from *Candida rugosa* in a concentration of 10 U/g of mixture, and the resulting mixture was subjected to selective transesterification at 30° C. for 16 hours to give an oil layer in a yield of 717 g. The reaction product was subjected to molecular distillation according to the conventional method, and the lauryl ester fractions collected were subjected to hydrolysis under the alkaline condition according to the conventional method to give the 9cis,11trans-CLA in a yield of 159 g (92.2% by weight).

Example 4

Male OLETF rats (7 weeks old), an animal model of non-insulin dependent diabetes mellitus, were assigned to three groups that were fed ad libitum with a semisynthetic diet (AIN-76) supplemented with 0.5% high linoleic safflower oil (Rinoru Oil Mills Co., Ltd.; control group), or a semisynthetic diet supplemented with 0.5% 9cis,11trans-CLA, and a semisynthetic diet supplemented with 0.5% 10trans,12cis-CLA for three weeks. The composition of the semisynthetic diets are presented in Table 1. The systolic blood pressure of rats was measured every two weeks by the indirect tail cuff method.

The systolic blood pressure in the control group was observed to raise along with the increase of the body weight (causing obesity). After 3 weeks of feeding with 0.5% 10trans,12cis-CLA group, systolic blood pressure was significantly suppressed compared with control group (Table 2). The changes of blood pressures in the feeding period of the CLA feeds are shown in FIG. 1. The fatty acid composition is shown in Table 3.

As regards the feeding period, the blood pressure of CLA group tends to lower as compared to that of the control group after one week of ingestion, so that hypotensive effect is exhibited in the feeding period of one week or more and the ingestion for the longer period will increase the effect.

It has been found from the above-described results that systolic blood pressure is lowered in rats fed with the 10trans,12cis-CLA. These results indicates that CLA in a relatively small amount exhibits the effect of lowering systolic blood pressure.

Example 5

Male SHR/Izm rats (5 weeks old) were assigned to two groups that were fed ad libitum with a semisynthetic diet (AIN-76) supplemented with 1.0% high linoleic safflower oil (Rinoru Oil Mills Co., Ltd.; control group), and a semisynthetic diet supplemented with 1.0% CLA mixture for four weeks (Table 4). The systolic blood pressure of rats was measured every week by the indirect tail cuff method using a Model MK-2000BP monitor (Muromachi Kikai, Tokyo, Japan). The CLA mixture was prepared in the same manner as in Example 1 (Table 5).

It was observed that the ingestion of CLA mixture tends to suppress the increase of blood pressure (Table 6).

Example 6

Male Zucker rats (7 weeks old) were assigned to two groups that were fed ad libitum with a semisynthetic diet (AIN-76) supplemented with 1.0% high linoleic safflower oil (Rinoru Oil Mills Co., Ltd.; control group), and a semisynthetic diet supplemented with 1.0% CLA mixture for eight weeks (Table 4). The systolic blood pressure of rats was measured every week by the indirect tail cuff method using a Model MK-2000BP monitor (Muromachi Kikai, Tokyo, Japan). It was observed in the group added with the CLA mixture that the increase of blood pressure was suppressed from six weeks of the feeding (Table 2).

The results of Examples 5 and 6 reveal the effect of suppressing the increase of blood pressure by the CLA mixture.

TABLE 1

Composition of experimental diets (AIN-76 type)

| Ingredient | Control group (g/kg of feed) | 9cis, 11trans-CLA group (g/kg of feed) | 10trans, 12cis-CLA group (g/kg of feed) |
|---|---|---|---|
| Casein | 200 | 200 | 200 |
| Corn starch | 150 | 150 | 150 |
| Cellulose | 50 | 50 | 50 |
| Mineral mixture (AIN76) | 35 | 35 | 35 |
| Vitamin mixture (AIN76) | 10 | 10 | 10 |
| DL-Methionine | 3 | 3 | 3 |
| Choline Bitartarate | 2 | 2 | 2 |
| Corn oil | 50 | 50 | 50 |
| High linoleic safflower oil | 5 | — | — |
| 9cis, 11trans-CLA | — | 5 | — |
| 10trans, 12cis-CLA | — | — | 5 |
| Sucrose | 495 | 495 | 495 |

TABLE 2

Effect of CLA on the blood pressure of rats

| | Control group | 9cis, 11trans-CLA group | 10trans, 12cis-CLA group |
|---|---|---|---|
| Initial value (mmHg) | 106 ± 4 | 103 ± 3 | 106 ± 4 |
| 1 Week (mmHg) | 131 ± 5 | 131 ± 3 | 125 ± 6 |
| 2 Weeks (mmHg) | 139 ± 5$^{ab}$ | 148 ± 4$^a$ | 128 ± 5$^b$ |
| 3 Weeks (mmHg) | 144 ± 3$^a$ | 154 ± 4$^a$ | 132 ± 3$^b$ |

Different superscript letters (a, b, ab) show significant differences at $p < 0.05$.

TABLE 3

Composition of fatty acids

| Ingredient | Control group (% by weight) | 9cis, 11trans-CLA group (% by weight) | 10trans, 12cis-CLA group (% by weight) |
|---|---|---|---|
| c16:0 | 6.3 | 0 | 0 |
| c18:0 | 2.5 | 0 | 0 |
| c18:1 | 16.8 | 2.1 | 0 |
| c18:2 | 72.6 | 1.2 | 0 |
| 9cis, 11trans-CLA | 0 | 92.2 | 3.1 |
| 10trans, 12cis-CLA | 0 | 3.3 | 95.7 |

TABLE 4

Feed composition mixture (AIN-76 type)

| Ingredient | Control group (g/kg of feed) | CLA mixture group (g/kg of feed) |
|---|---|---|
| Casein | 200 | 200 |
| Cornstarch | 150 | 150 |
| Cellulose | 50 | 50 |
| Mineral blend (AIN76) | 35 | 35 |
| Vitamin blend (AIN76) | 10 | 10 |
| DL-Methionine | 3 | 3 |
| Choline Bitartarate | 2 | 2 |
| Corn oil | 50 | 50 |
| High linoleic safflower oil | 10 | 0 |
| CLA mixture | 0 | 10 |
| Sucrose | 495 | 495 |

TABLE 5

Composition of fatty acids

| Ingredient | CLA mixture (% by weight) |
|---|---|
| C18:1 | 2.2 |
| C18:2 | 0.9 |
| 9-cis-11-trans-CLA | 46.0 |
| 10-trans-12-cis-CLA | 47.3 |
| Others (fatty acids) | 3.6 |

TABLE 6

Effect of CLA mixture on the blood pressure of SHR/Izm rats

|  | Control group | CLA mixture group |
|---|---|---|
| Initial value (mmHg) | 109 ± 2 | 111 ± 2 |
| 4 Weeks (mmHg) | 163 ± 2 | 155 ± 3 |
| Change (%) | 50.3 ± 3.0 | 39.6 ± 2.0* |

Value with asterisk is significantly different from control group at $p < 0.05$.

<Exemplary Blending of Foods and the Like>

| Mayonnaise | (% by weight) |
|---|---|
| CLA | 1.0 |
| Fats and oils | 69.0 |
| Yolk | 15.0 |
| Vinegar | 13.0 |
| Salt | 2.0 |

<Exemplary Formulation of Pharmaceutical>

CLA powder prepared by pulverizing CLA was used for producing tablets with the following formula according to the conventional method.

|  | (% by weight) |
|---|---|
| CLA Powder | 40.0 |
| Crystalline cellulose | 4.0 |
| Sucrose ester | 2.0 |
| Shellac | 2.6 |
| White sugar | 30.0 |
| Talc | 0.1 |
| Calcium carbonate | 0.5 |
| Lactose | 18.7 |
| Titanium oxide | 0.1 |
| Pullulan | 0.04 |
| Gelatin | 1.2 |
| Guar gum | 0.2 |
| Caramel pigment | 0.56 |

As described above, according to the present invention it is possible to provide feeds, drinks, foods, health food supplements, and pharmaceuticals which can be used for the prophylaxis or amelioration of hypertension to improve physical constitution and finally led to prophylaxis or amelioration of life style-related diseases by using the conjugated fatty acids.

Thus, it would be understood to be surprising that the conjugated fatty acids (particularly, conjugated linoleic acid) exhibit the effects described above.

What is claimed is:

1. An ameliorating agent of hypertension comprising a conjugated linoleic acid as an effective ingredient.

2. An ameliorating agent of hypertension according to claim 1, wherein the conjugated linoleic acid is in the form of a free fatty acid, salt, ester, fatty acid derivative, or a mixture of the two or more thereof.

3. An ameliorating agent of hypertension according to claim 1, wherein the conjugated linoleic acid comprises 5% by weight or more of the-10trans,12cis-isomer.

4. A feed comprising the conjugated linoleic acid or the agent according to claim 1.

5. A food or drink comprising the conjugated linoleic acid or the agent according to claim 1.

6. A health food supplement comprising the conjugated linoleic acid or the agent according to claim 1.

7. A pharmaceutical comprising the conjugated linoleic acid or the agent according to claim 1.

8. A method for ameliorating of hypertension in a mammal, which comprises administering to the mammal an effective amount of a conjugated linoleic acid for preventing or ameliorating of hypertension in the mammal.

9. A method according to claim 8, wherein the conjugated linoleic acid is in the form of a free fatty acid, salt, ester, fatty acid derivative, or a mixture of the two or more thereof.

10. A method according to claim 8, wherein the conjugated linoleic acid is in the form of a feed.

11. A method according to claim 8, wherein the conjugated linoleic acid is in the form of a food and drink.

12. A method according to claim 8, wherein the conjugated linoleic acid is in the form of a health food supplement.

13. A method according to claim 8, wherein the conjugated linoleic acid is in the form of a pharmaceutical.

14. An ameliorating agent of hypertension according to claim 1, wherein the conjugated linoleic acid comprises 40% by weight or more of the-10trans,12cis-isomer.

15. An ameliorating agent of hypertension according to claim 1, wherein the conjugated linoleic acid comprises 85% by weight or more of the-10trans,12cis-isomer.

* * * * *